United States Patent [19]

Cook

[11] Patent Number: 4,867,464
[45] Date of Patent: Sep. 19, 1989

[54] CHILD RESTRAINING SAFETY BELT OR HARNESS

[76] Inventor: Kenna M. Cook, 13123 Flying Squirrel Ct., Bayonet Point, Fla. 34669

[21] Appl. No.: 302,035

[22] Filed: Jan. 26, 1989

Related U.S. Application Data

[63] Continuation-in-part of Ser. No. 102,836, Sep. 30, 1987, abandoned.

[51] Int. Cl.⁴ .................... B62B 11/00; B62B 9/24
[52] U.S. Cl. ........................ 280/33.993; 297/484
[58] Field of Search ............ 280/33.993, 33.992, 280/33.991, 290, 801, 808; 297/487, 484; 119/96; 128/874, 876

[56] References Cited

U.S. PATENT DOCUMENTS

| | | | |
|---|---|---|---|
| 1,310,958 | 7/1919 | O'Connor | 119/96 |
| 1,574,672 | 2/1926 | McCarroll-Doull | 128/134 |
| 2,675,557 | 4/1954 | Kempner, Jr. | 128/134 |
| 3,077,292 | 2/1963 | Gehrke | 119/96 X |
| 3,088,438 | 5/1963 | Oliphant | 119/96 |
| 3,350,136 | 10/1967 | Allen | 280/33.993 |
| 3,612,605 | 10/1971 | Posey, Jr. | 297/484 |
| 4,108,170 | 8/1978 | Spann | 128/134 |
| 4,132,230 | 1/1979 | Ladd | 128/134 |
| 4,550,800 | 11/1985 | Dietrich | 280/33.993 |
| 4,637,622 | 1/1987 | Burgard | 280/33.993 |
| 4,666,017 | 5/1987 | Zimmerman | 119/96 X |
| 4,667,624 | 5/1987 | Smith | 119/96 |
| 4,699,090 | 10/1987 | Voorhees | 119/96 |

FOREIGN PATENT DOCUMENTS

| | | | |
|---|---|---|---|
| 1124587 | 8/1968 | United Kingdom | 297/484 |
| 1132577 | 11/1968 | United Kingdom | 297/484 |
| 1506926 | 4/1978 | United Kingdom | 297/484 |

Primary Examiner—Charles A. Marmor
Assistant Examiner—Tamara L. Finlay
Attorney, Agent, or Firm—Stanley M. Miller

[57] ABSTRACT

A safety device that restrains very small children to a shopping cart seat and that serves as a harness when the child is not seated in the seat. A middle strap member overlies the child's stomach and wraps around part of the back of a shopping cart seat. The opposite ends of the middle strap member are releasably fastened together behind the child's back. A pair of shoulder strap members are secured at a first end to the middle strap member and overlie the child's shoulders. A second end of each shoulder strap member is fixedly secured to a flat material that is looped to carry a pair of large "D" ring members to which is releasably secured a bottom strap member that extends from the middle strap member, under the shopping cart seat, to the "D" ring members to unite the shoulder strap members to the bottom strap member. A tether member is secured to the device to harness the child when the child is not in the shopping cart seat.

4 Claims, 3 Drawing Sheets

CHILD RESTRAINING SAFETY BELT OR HARNESS

CROSS-REFERENCE TO RELATED APPLICATIONS

This disclosure is a continuation-in-part of a co-pending disclosure filed by the present inventor on Sept. 30, 1987, bearing Ser. No. 07/102,836, now abandoned.

BACKGROUND OF THE INVENTION

1. Field of the Invention

This invention relates, generally, to safety devices having utility in strapping young children to seats. More particularly, it relates to a safety belt means that retains a young child in a shopping cart of the type having a foldable child's seat.

2. Description of the Prior Art

Shopping carts are provided with foldable seats to help adult shoppers complete their shopping chores without needing to a hire a baby sitter. Typically, the foldable seat is designed to be folded and stored out of the way when the shopper is not accompanied by a small child.

When the shopper is accompanied by a small child, the seat is unfoldable and the child is seated therein. The back of the seat faces the adult so that the child rides facing the adult pushing the cart, i.e., the child does not face in the direction of shopping cart travel.

Leg openings are provided at the front of the cart so that the child can sit comfortably upon the seat.

The seats are not provided with safety belts. Accordingly, a small warning against leaving the child unattended is usually printed on the seat. Due to the height of the seat and the hardness of a grocery store floor, an active child who is left unattended for even a brief period of time can fall from the seat and suffer injury.

Seat belts in general are of course well known but few safety devices having utility in the environment of a shopping cart seat have been developed.

As more fully set forth in the cross-referenced disclosure, earlier patents to O'Connor, Gehrke, McCarroll-Doull, Voorhees, Smith, Posey, Jr. and Ladd all show earlier harnesses; none of them have specific utility in connection with children and shopping cart seats.

O'Connor discloses a harness device that includes a middle section, shoulder straps and a bottom strap that are connected to one another in a manner different from the present invention.

Gehrke shows a tether strap that connects to a "D" ring, but the "D" ring is not affixed to a shoulder strap piece of the type disclosed herein. Instead, the Gehrke "D" ring encircles a pair of criss-crossing shoulder straps, which type of shoulder straps are not disclosed herein.

The same observation applies to the Smith disclosure.

McCarroll-Doull shows a toy strap.

Posey, Jr. shows the use of straps that at least partially wrap around a chair, but his construction includes no bottom strap.

VELCRO (trademark) hook and loop fastening means, snap fasteners, and padded material, are shown by Posey, Jr., Ladd, and Voorhees, respectively.

A need remains extent for a child safety belt and harness having utility in the environment of a shopping cart foldable seat.

SUMMARY OF THE INVENTION

The longstanding but unfulfilled need for a child safety belt having utility in connection with shopping cart seats is now fulfilled by the present construction of a safety belt that fits over, under and around the seat and a child seated thereon.

An elongate, flexible middle strap member has a medial section that overlies the stomach of a child seated on a shopping cart seat when the invention is in use. The opposite ends of the middle strap member extend through vertical bars that form the back section of the seat and releasably connect to one another behind the child. Thus, the child cannot release the middle strap member.

A pair of elongate, flexible shoulder strap members are employed to support the middle strap member.

Each shoulder strap member has a first or forward end fixedly secured to the middle strap member on that part of the middle strap member that overlies the child's stomach, i.e., the forward end of each shoulder strap member is secured to the front part of the inventive device.

The respective forward ends of the shoulder strap members are positioned on opposite sides of the center of the middle strap member, in equidistantly spaced relation thereto. The shoulder strap members are disposed in converging relation to one another so that a second, or rearward end of the first shoulder strap member overlies the second, rearward end of the second shoulder strap member when the strap members are operatively disposed in overlying relation to the child's shoulders.

The respective rearward ends of the shoulder strap members are fixedly secured to a flat piece of material termed herein the shoulder strap connecting means.

The shoulder strap connecting means has a loop formed therein; the loop captures a pair of large "D" ring members.

An elongate, flexible bottom strap member has a first end fixedly secured to the medial section of the middle strap member and a second end thereof is releasably captured by the large "D" ring members carried by the shoulder strap connecting means.

Thus, when the child is seated in a shopping cart seat, the bottom strap member is brought under the bench part of the shopping cart seat and the distal free end thereof is secured to the large "D" rings carried by the shoulder strap connecting means behind the child's back.

Thus, all connecting means are positioned behind the child's back. Since the back part of the shopping cart seat is high, the child cannot reach around to the back of the device to release any of the attachment means.

The shoulder strap connecting means also carries a tab means that captures a small "D" ring member. An elongate tether strap member has a first end adapted to be grasped by an adult and a second end adapted to engage the small "D" ring so that the safety belt can be used as a harness when the child is not seated in the shopping cart seat.

The primary object of this invention is to promote safety by providing a device that will secure even the most active of young children to a shopping cart seat.

Another important object is to provide a safety belt having all of its releasable fastening means positioned at a location that can not be reached by the child wearing the safety belt.

Another object is to provide a safety belt that is of simple construction so that it can be quickly deployed into its operative configuration in restraining relation to a child seated on a foldable shopping cart.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
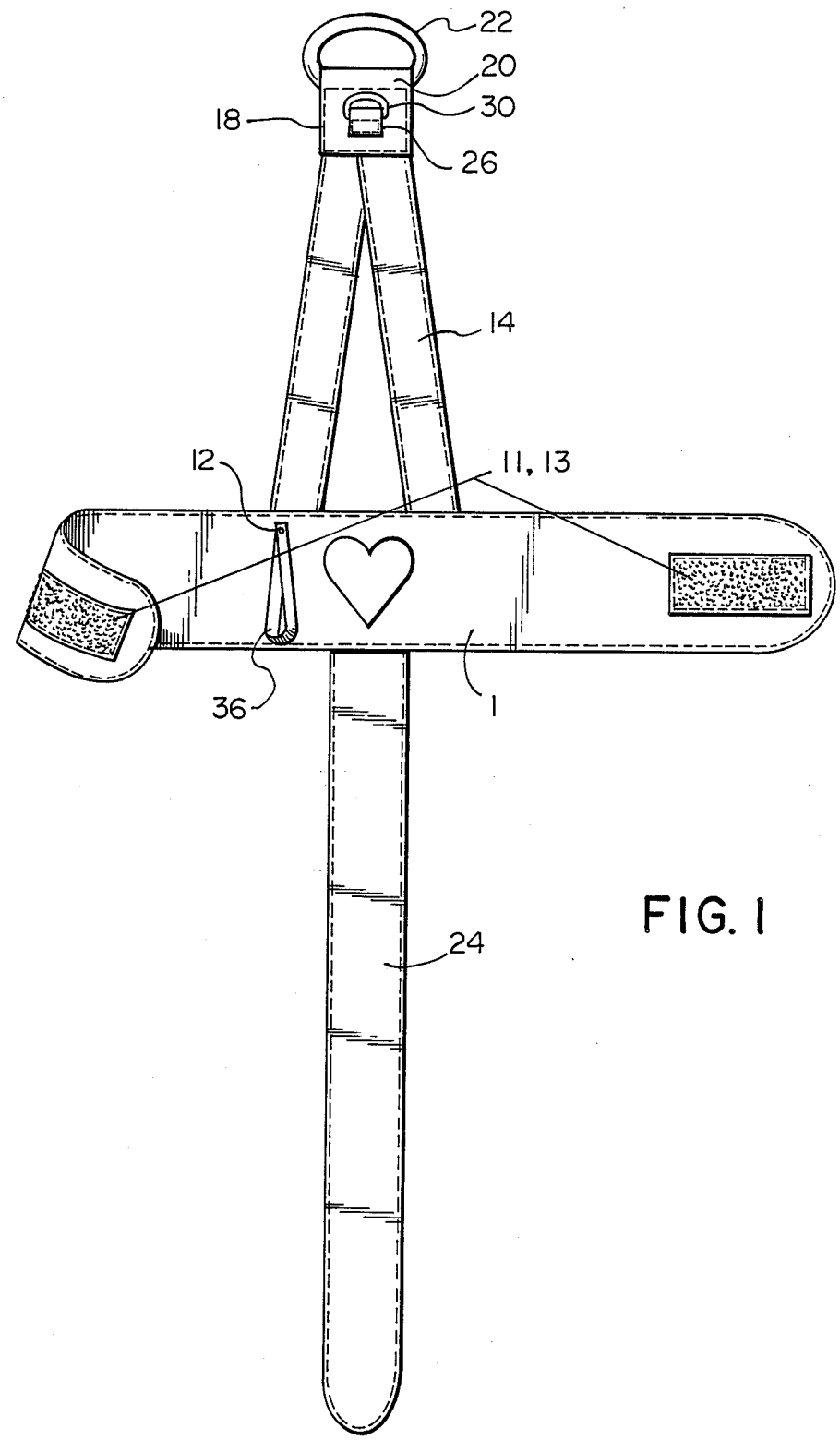
FIG. 1 is a front elevational view of the novel device.

Refering now to FIG. 1, it will there be seen that the novel apparatus is denoted as a whole by the reference numeral 10.

Safety belt 10 includes a flexible, elongate middle strap member 12, a pair of elongate, flexible, shoulder strap members 14, 16, a shoulder strap connecting means 18, a loop means 20 formed in an edge of connecting means 18, a pair of "D" ring members collectively denoted 22 captured thereby, and a flexible, elongate bottom strap member 24.

Figure 3:
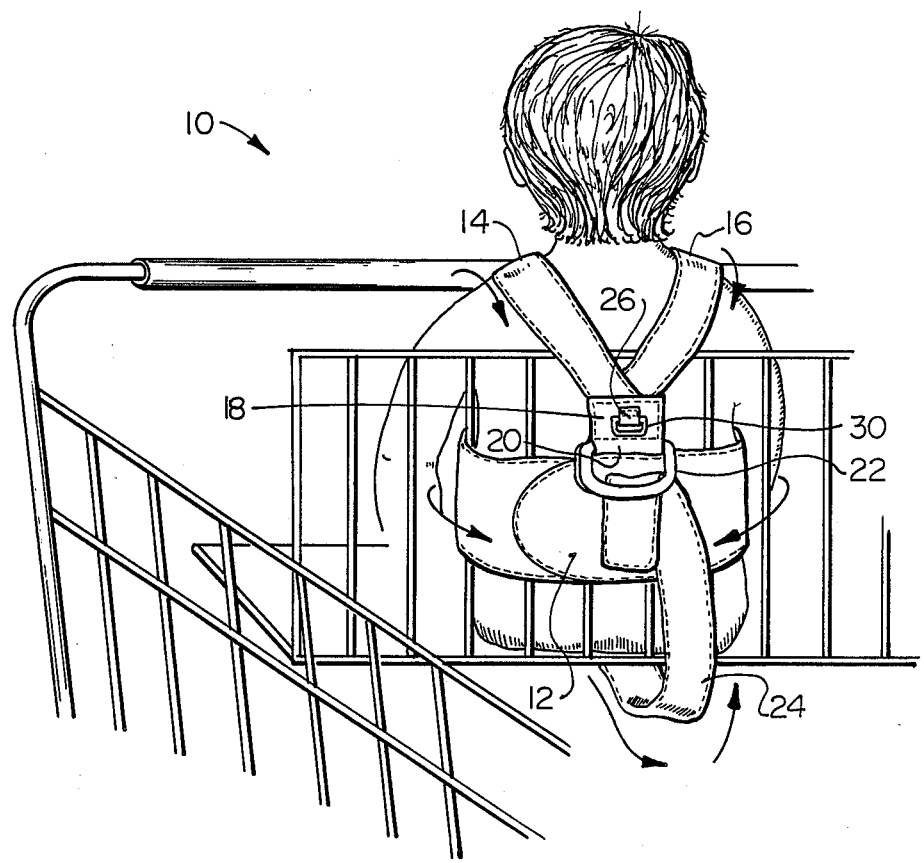
FIG. 3 is a perspective view of a child seated in a shopping cart seat with the present inventive apparatus being disposed in its operative configuration.
Figure 4:
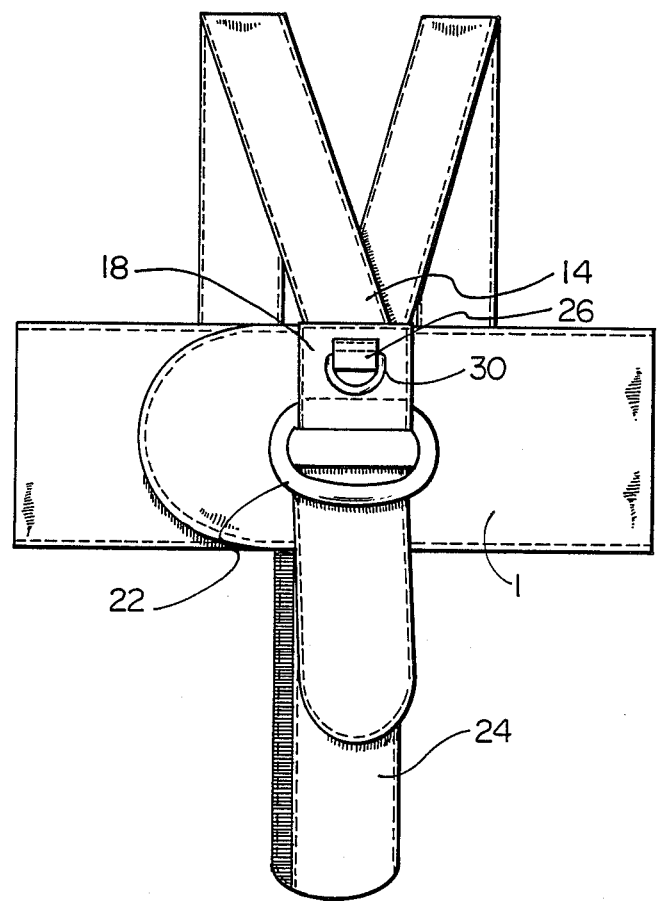
FIG. 4 is a back view of the invention in a fastened, operative configuration.

Suitable hook and loop fastening means 11, 13 such as VELCRO (trademark) are provided on a middle strap member 12 as shown in FIG. 1 to releasably secure the opposite ends thereof to one another when device 10 is deployed as depicted in FIG. 3.

Each shoulder strap member 14, 16 has a forward end fixedly secured to middle strap member 12, on equidistantly spaced opposite sides of the center of the middle strap member 12. Importantly, the shoulder strap members are disposed in converging relation to one another so that the respective distal ends thereof are disposed in overlapping relation to one another.

More particularly, the second or rearward end of shoulder strap member 14 overlies the second or rearward end of shoulder strap member 16, or vice versa. The rearward ends of the shoulder strap members 14, 16 are secured to one another and to the shoulder strap connecting means 18 behind the child when the device is operatively deployed as depicted in FIG. 3.

The distal free end of bottom strap member 24 is captured by the "D" ring members 22 when the device is in use; thus, all of the releasable connections of strap members are made behind the back of the child.

As FIG. 3 shows, the back part of a typical shopping cart seat is quite high in relation to a small child; thus, due to the short dimensions of a child's arms, the child cannot reach over the high back and release the connections.

The shoulder strap members 14, 16 cooperate with the bottom strap member 24 which is passed under the bench part of the shopping cart seat as shown in FIG. 3 to prevent the child from standing.

The middle strap member 12, which follows a path of travel around at least one of the vertical bars in the back part of the shopping cart seat as shown in FIG. 3 serves to prevent the child from falling over to the left or right.

Additional features of the invention include a small tab member 26 which has a loop 28 formed therein to capture a small "D" ring member 30 therein. The small tab member is fixedly secured to the shoulder strap connecting means 18.

Figure 2:
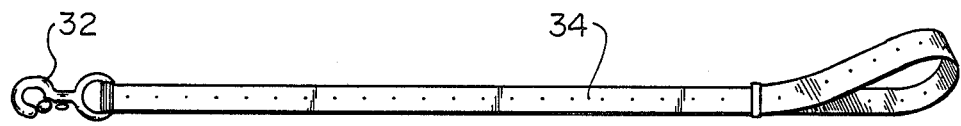
FIG. 2 is a front elevational view of a tether strap that forms a part of the invention.

When the device is being used as a harness, i.e., when it is not being used as a safety belt as in FIG. 3, the distal end 32 of elongate, flexible tether member 34 of FIG. 2 is releasably secured to the small "D" ring member 30 by means of a suitable fastening means as illustrated. Thus, an adult grasping the proximal or handle end of tether member 34 will be able to restrain the child when the child is free of the shopping cart seat.

For very active small children, it is advisable to attach the fastening means 32 of the tether strap member 34 to the small "D" ring 30 prior to removing the child from the shopping cart seat.

A toy strap member 36 may be secured to the front of middle strap member 12 as shown in FIG. 1. The toy strap 36 prevents a toy from falling far when released by a child. The toy strap 36 is openable and closable by suitable means to enable the toy held thereby to be changed from time to time.

It will thus be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A device for restraining young children in a shopping cart of the type having a foldable seat, including a bench section and a back section, comprising:
   an elongate, flexible middle strap member having opposite ends and a center;
   fastening means for releasably securing together said opposite ends of said middle strap member;
   said middle strap member having a preselected length sufficient to wrap around a child's torso and a preselected part of the back section of said shopping cart seat;
   said opposite ends of said middle strap member being releasably securable to one another behind the back of a child seated in said shopping cart seat;
   a pair of elongate, flexible shoulder strap members;
   each of said shoulder strap members having a first end fixedly secured to said middle strap member, said respective first ends being disposed on opposite sides of the center of said middle strap member in equidistantly spaced relation thereto;
   said shoulder strap members disposed in converging relation to one another so that a second end of a first strap member overlies a second end of a second strap member;
   a shoulder strap connecting means disposed where the second ends of said first and second strap members converge, each of said second ends being fixedly secured to said shoulder strap connecting means;

a loop means formed in said shoulder strap connecting means;

a pair of large "D" ring members, each of said "D" ring members having a linear in configuration portion and an arcuate portion;

each of said linear in configuration portions of said large "D" ring members being captured by said loop means; and an elongate, flexible bottom strap member having a first end fixedly secured to said middle strap member at the center thereof and a second end releasably securable to said large "D" ring members behind said child's back;

whereby a medial part of said middle strap member is placed in overlying relation to the stomach of a child seated in a shopping cart seat, said shoulder strap members are passed over the child's head so that said shoulder strap connecting means is positioned in overlying relation to the child's back, said bottom strap member is passed under the bench section of the shopping cart seat, said middle strap member is passed around at least a portion of said shopping cart back and fastened behind the child's back, and said free end of said bottom strap is brought upwardly behind the child to said large "D" ring members and fastened to said large "D" ring members to unite said shoulder strap members and said bottom strap member;

whereby all fastening means are out of the reach of a small child seated in a shopping cart seat.

2. The device of claim 1, further comprising a tab member fixedly secured to said shoulder strap connecting means, a loop means formed in said tab member, and a small "D" ring member captured by said loop means.

3. The device of claim 2, further comprising an elongate, flexible tether strap member having a handle means formed on a first end thereof and a fastening means secured to a second end thereof, said tether strap fastening means for releasably engaging said small "D" ring member so that the device has utility as a child harness when the child is not positioned in said shopping cart seat.

4. The device of claim 3, further comprising a toy strap member to which a toy may be releasably secured, said strap member being provided in the form of a loop means fixedly secured to said middle strap member near the center thereof.

* * * * *